(12) United States Patent
Ryoo

(10) Patent No.: US 11,604,124 B2
(45) Date of Patent: Mar. 14, 2023

(54) SOLUTION COMPOSITION FOR EXTRACTING AVAILABLE PHOSPHATE, AVAILABLE SILICATE AND CATION EXCHANGE IN SOIL

(71) Applicant: ANDONG NATIONAL UNIVERSITY INDUSTRY—ACADEMIC COOPERATION FOUNDATION, Gyeongsangbuk-do (KR)

(72) Inventor: Keon Sang Ryoo, Gyeongsangbuk-do (KR)

(73) Assignee: ANDONG NATIONAL UNIVERSITY INDUSTRY—ACADEMIC COOPERATION FOUNDATION, Gyeongsangbuk-do (KR)

( * ) Notice: Subject to any disclaimer, the term of this patent is extended or adjusted under 35 U.S.C. 154(b) by 160 days.

(21) Appl. No.: 17/133,034

(22) Filed: Dec. 23, 2020

(65) Prior Publication Data

US 2021/0199548 A1    Jul. 1, 2021

(30) Foreign Application Priority Data

Dec. 26, 2019    (KR) .................. 10-2019-0175028

(51) Int. Cl.
  *G01N 1/40*     (2006.01)
  *G01N 21/25*    (2006.01)
  *G01N 33/24*    (2006.01)
  *G01N 31/22*    (2006.01)

(52) U.S. Cl.
  CPC .......... *G01N 1/4055* (2013.01); *G01N 21/25* (2013.01); *G01N 31/22* (2013.01); *G01N 31/221* (2013.01); *G01N 33/24* (2013.01); *G01N 1/4044* (2013.01); *G01N 2001/4061* (2013.01); *G01N 2033/245* (2013.01)

(58) Field of Classification Search
  CPC ...... G01N 1/4055; G01N 31/22; G01N 33/24; G01N 1/4044; G01N 2001/4061; G01N 2033/245; G01N 21/78
  See application file for complete search history.

(56) References Cited

FOREIGN PATENT DOCUMENTS

| CN | 101297197 B | * | 10/2012 | ............. G01N 21/78 |
|---|---|---|---|---|
| KR | 1020010025333 A | | 4/2001 | |
| KR | 100295183 B1 | * | 10/2001 | ............. G01N 31/22 |
| KR | 1003421990000 B1 | | 6/2002 | |

* cited by examiner

*Primary Examiner* — Benjamin R Schmitt
(74) *Attorney, Agent, or Firm* — Berkeley Law & Technology Group, LLP

(57) ABSTRACT

Disclosed is a leaching solution composition for extracting available phosphate in soil, the composition including 100 parts by weight of a leaching solution containing acetic acid, lactic acid, ammonium fluoride, ammonium sulfate, and sodium hydroxide, of which the weights are 110% of the weights of constituent ingredients of a leaching solution for extracting available phosphate in soil, used in the Lancaster method and 0.001 parts by weight of a bromocresol green indicator.

1 Claim, 2 Drawing Sheets

(Apparatus for manufacturing leaching solution)

(Three types of leaching solutions)

SOLUTION COMPOSITION FOR EXTRACTING AVAILABLE PHOSPHATE, AVAILABLE SILICATE AND CATION EXCHANGE IN SOIL

BACKGROUND OF THE INVENTION

1. Field of the Invention

The present disclosure relates to a leaching solution used for leaching tests of inorganic elements that are dissolved out of soil.

2. Description of the Prior Art

Leaching solutions prepared according to official testing methods have been used to analyze elements that are dissolved and extracted from farmland among inorganic element components contained in the farmland. Examples of the leaching solutions are: a leaching solution for available silicate to extract silicate; a leaching solution for available phosphate to extract phosphate; and a leaching solution for cation exchange to extract calcium, magnesium, sodium, and potassium. These three types of leaching solutions are used for analysis in order to check farmland conditions before dressing of a fertilizer (farms supply the soil with ingredients in which the fertilizer is prone to deficient, especially, nitrogen, phosphate, and potassium fertilizers, to promote crop growth or increase yields or quality).

The three types of leaching solutions need to be precisely pH-adjusted for each manufacturing process. The pH of leaching solutions needs to be precisely adjusted during the preparation of reagents, and the manufactured leaching solutions need to be not denatured during the period of use. However, in most cases, the precise adjustment of pH is difficult and the adjusted pH is changed over the time, resulting in difficulty in each time of analysis. Moreover, when the pH of the manufactured leaching solutions is changed, such a change cannot be distinguished with the naked eye, and as a result, the denatured leaching solution is used as it is, resulting in incorrect analysis values. Moreover, different pH values result in different analysis values, may lead to different fertilizer dressing prescriptions, and thus the change of pH needs to be carefully monitored. In addition, during the preparation of reagents, exposure to harmful reagents (badly smelling ammonia water, acetic acid, and the like) always occurs, and thus there always exist dangers.

PRIOR ART DOCUMENTS

Patent Documents (Patent Document 001) Korean Patent Registration No. 10-0342199 (14 Jun. 2002)
(Patent Document 0002) Korean Patent Publication No. 10-2001-0025333 (6 Apr. 2001)

SUMMARY OF THE INVENTION

The present disclosure has been made in order to solve the above-mentioned problems in the prior art, and an aspect of the present disclosure is to provide a leaching solution, of which the pH is not changed even during long-term storage and the pH change, if any, can be distinguished with the naked eye.

In accordance with an aspect of the present disclosure, there is provided, as a solution composition for extracting available phosphate in soil, a leaching solution composition for extracting available phosphate in soil, the composition including: 100 parts by weight of a leaching solution containing acetic acid, lactic acid, ammonium fluoride, ammonium sulfate, and sodium hydroxide, of which the weights are 110% of the weights of acetic acid, lactic acid, ammonium fluoride, ammonium sulfate, and sodium hydroxide, respectively, contained in a leaching solution for extracting available phosphate in soil, used in the Lancaster method; and 0.001 parts by weight of a bromocresol green indicator.

In accordance with another aspect of the present disclosure, there is provided, as a solution composition for extracting available silicate in soil, a leaching solution composition for extracting available silicate in soil, the composition including: 100 parts by weight of a leaching solution containing sodium acetate and acetic acid, of which the weights are 110 wt % of the weights of sodium acetate and acetic acid, respectively, contained in a leaching solution for extracting available silicate in soil, used in the 1N-NaOAc method; and 0.001 parts by weight of a methyl orange indicator.

In accordance with still another aspect of the present disclosure, there is provided, as a solution composition for extracting exchangeable cations in soil, a leaching solution composition for extracting exchangeable cations in soil, the composition including: 100 parts by weight of a leaching solution containing ammonium hydroxide and acetic acid, of which the weights are 110% of the weights of ammonium hydroxide and acetic acid, respectively, contained in a leaching solution for extracting exchangeable cations in soil, used in an ammonium acetate method in cation exchange capacity (CEC) analysis; 0.001 parts by weight of a phenolphthalein indicator; and 0.001 parts by weight of a bromocresol purple indicator.

According to the present disclosure, the solution composition for extracting available phosphate, available silicate, or exchangeable cations in soil shows no pH change even during the long-term storage, and the pH change, if any, can be distinguished with the naked eye.

BRIEF DESCRIPTION OF THE DRAWINGS

The above and other aspects, features and advantages of the present disclosure will be more apparent from the following detailed description taken in conjunction with the accompanying drawings, in which.

DETAILED DESCRIPTION OF THE EXEMPLARY EMBODIMENTS

Figure 1:
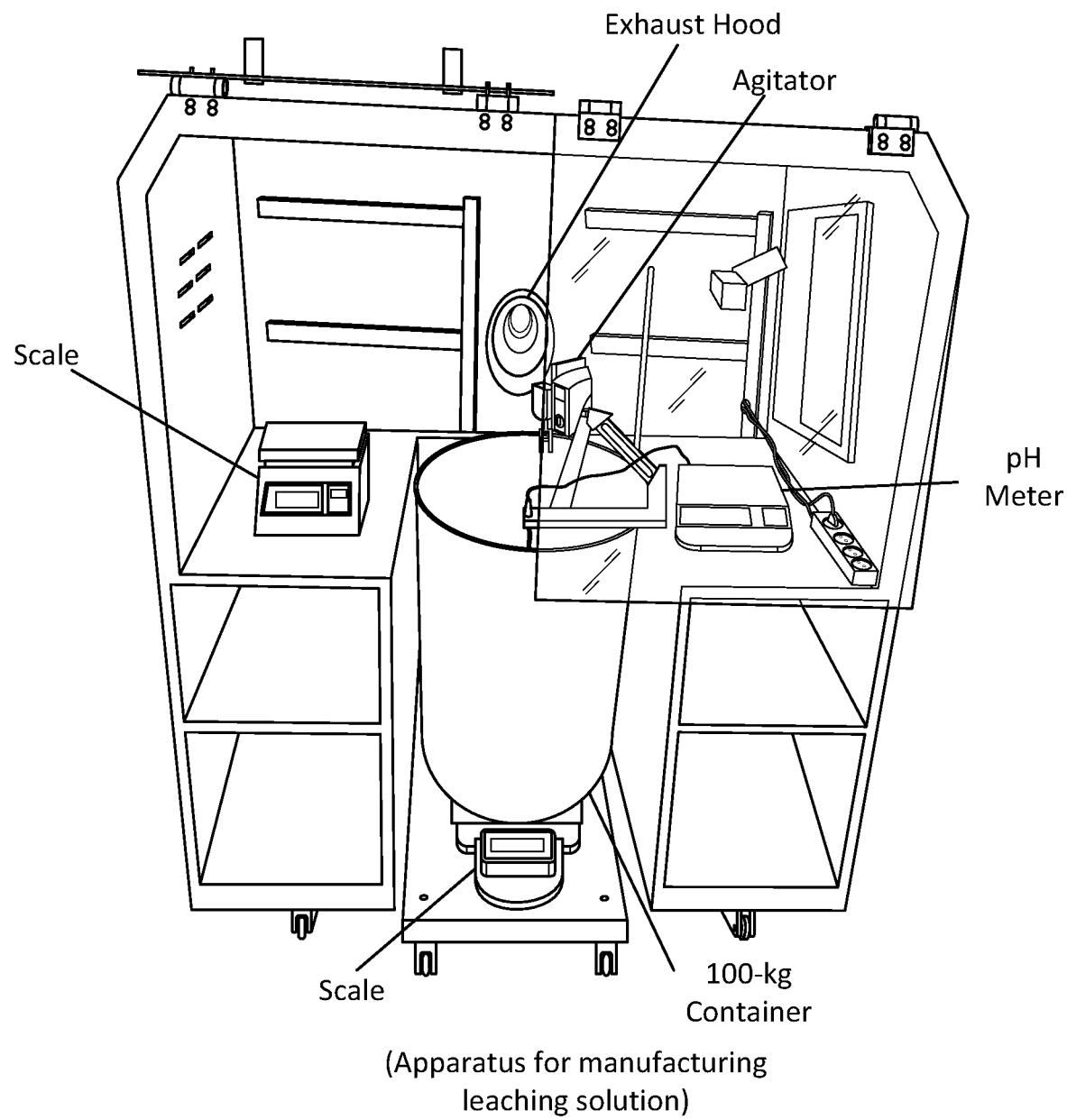
FIG. 1 shows photographs depicting a manufacturing apparatus used in the manufacturing of three types of leaching solutions in the present examples.
Figure 2:
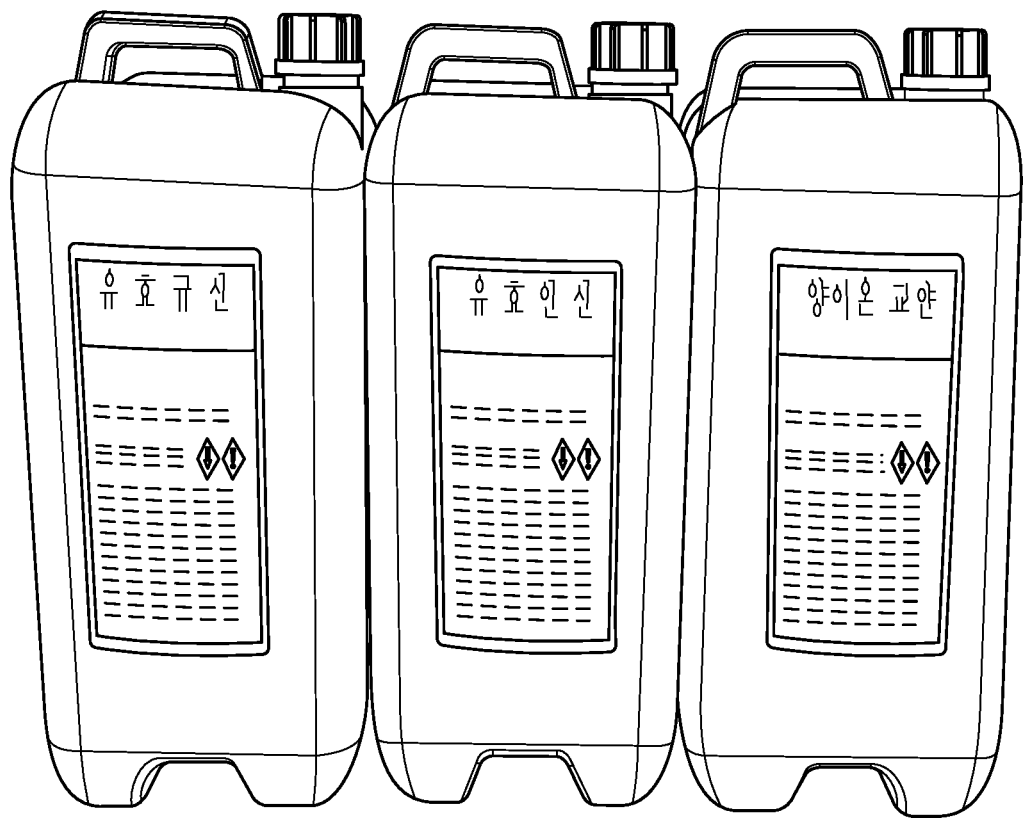
FIG. 2 shows three types of leaching solutions included in containers, the leaching solutions being manufactured in the present examples.

In the following description, a detailed description of known functions and configurations incorporated herein will be omitted when it may obscure the subject matter of the present disclosure.

The exemplary embodiments according to the subject matter of present disclosure may be diversely modified and may have various forms, and thus specific exemplary embodiments are illustrated in the drawings and are described in detail in the detailed description or application. However, it is to be understood that the present disclosure is not limited to a specific exemplary embodiment but includes all modifications, equivalents, and substitutions without departing from the scope and spirit of the present disclosure.

The terms used herein are not intended to limit the present disclosure but to describe specific exemplary embodiments. A singular expression includes a plural expression, unless otherwise specified. Herein, it is to be understood that the terms such as "include" and "have" are intended to designate a presence of characteristic, number, step, operation, element, component, or a combination thereof, and not to preclude a presence or a possibility of adding one or more other characteristic, numbers, steps, operations, elements, components, or a combination thereof.

Hereinafter, the present disclosure will be described in detail with reference to exemplary embodiments. However, the corresponding exemplary embodiments may be modified into several other forms, and the scope of the present disclosure is not to be construed to being limited to the exemplary embodiments described below, and the corresponding exemplary embodiments are provided for the purpose of more fully explaining the present disclosure to those having average knowledge in the art.

EXAMPLES

Specifically, a leaching solution for available phosphate, a leaching solution for available silicate, and a leaching solution for exchangeable cations are prepared in 100 kg/batch units. In a case where a leaching solution is prepared at less than 50 kg per batch, the volume of the leaching solution is small and thus reagents to be added are difficult to accurately quantify. In a case where a leaching solution is prepared at more than 200 kg/batch, the volume of the leaching solution is large and thus the leaching solution is difficult to handle. The pH change is prevented during the storage for a long period by adding reagents at weights of 1.1 times the reagent weights required by an existing official testing method. If reagents are quantified as prescribed in the official testing method and added to manufacture a leaching solution for available phosphate, a leaching solution for available silicate, and a leaching solution for exchangeable cations, the leaching solutions are difficult to store for a long period of time due to severe changes of pH. If reagents are added at quantitative amounts of 1.2 times greater than those prescribed in the official testing method to manufacture the leaching solutions, the reagents are excessively used, causing an increase in costs, and silicate, phosphate, calcium, magnesium, potassium, and sodium to be extracted tend to be partially extracted at low levels. The quantitative amounts of the reagents are most preferably 1.1 times the amounts prescribed in the official testing method.

To efficiently produce the leaching solutions, each of the reagents was divisionally stored on a basis of the weight of the reagent to be consumed by 100 kg production standard, and then in the manufacturing of the leaching solutions, the divisionally stored reagents were directly added to distilled water without separate reagent weighing, thereby mass-producing desired leaching solutions.

The divided weights for the three-type leaching solutions are as described in Tables 1 to 3 below. The weights of the reagents shown in each table were 1.1 times the weights prescribed in the official testing method, respectively, and previously divided several portions for each of the reagents were secured, thereby achieving accurate pH values of the leaching solutions as needed. A manufacturing apparatus (stainless steel) capable of producing 100 kg of a leaching solution was fabricated as shown in FIG. 1. The Sirocco fan was installed at the back side of the manufacturing apparatus so as to discharge harmful gas generated in the manufacturing apparatus. In addition, a fully transparent window was installed for safety during reactions for manufacturing a leaching solution, so that the weights of reagents and the volume of the manufactured leaching solution can be directly monitored inside the apparatus. An agitator configured to agitate a leaching solution when the leaching solution is dissolved and mixed was installed such that the agitator has a horse power two times higher than the existing capacity. The agitator was installed such that the rotation rpm could be observed in real time. A pH meter was fixed within the manufacturing apparatus such that the final pH of the leaching solution can be observed always, and adjustment by the pH meter was also performed within the manufacturing apparatus.

1. Preparation of Leaching Solution Composition for Extracting Available Phosphate in Soil As shown in Table 1 below, for the manufacturing of 100 kg of a leaching solution for available phosphate, 94,000 g of distilled water was first added into a 120-L reactor, and then 2310 g of acetic acid (CH3COOH), 1650 g of lactic acid (CH3CH(OH)COOH), 121.0 g of $NH_4F$, 733.15 g of $(NH_4)_2SO_4$, and 935 g of NaOH were added, followed by agitation at 100 rpm for 30 minutes, and then the pH was adjusted to 4.25 by using acetic acid and NaOH. In addition, 1 g of a bromocresol green indicator was dissolved in 100 g of ethanol and 100 g of distilled water, and then added together into the 120-L reactor, followed by further agitation for 1 minute, thereby manufacturing a leaching solution for available phosphate. The pH of the leaching solution for available phosphate was adjusted to 4.25±0.05, and for color distinguishment, 0.001 parts by weight of a bromocresol green acid-base indicator was added relative to the entire weight (100 parts by weight) of the manufactured leaching solution for available phosphate. The bromocresol green indictor is characterized by showing an evident color change in a pH range of 4.25±0.05. The leaching solution for available phosphate, to which the indicator has been added, exhibits a blue-green color, turns into dark green if contaminated or denatured to have a pH of 4.25 or lower and thus be acidic, and turns into dark blue if contaminated or denatured to have a pH of 4.25 or higher and thus be basic. When the bromocresol green indicator is added in less than 0.001 parts by weight, the color of the leaching solution becomes thin, resulting in difficulty in color distinguishment with the naked eye. When the bromocresol green indicator is added in more than 0.001 parts by weight, the color of the leaching solution becomes thick, which acts an obstacle in analysis. The concentration of the bromocresol green indicator is most preferably 0.001 parts by weight.

The leaching solution for available phosphate exhibits a green-blue color at a normal state, exhibits a green color when contaminated by an acid, and exhibits a blue color when contaminated by a base. Therefore, the normal and contaminated states of the leaching solution for available phosphate can be distinguished by colors.

TABLE 1

| Based on 100 kg of solution manufacturing | | |
|---|---|---|
| Leaching solution | Reagent | Amount |
| Leaching solution for available phosphate | Acetic acid ($CH_3COOH$) | 2310 g |
| | Lactic acid ($CH_3CH(OH)COOH$) | 1650 g |
| | $NH_4F$ | 121.0 g |
| | $(NH_4)_2SO_4$ | 733.15 g |
| | NaOH | 935 g | cf. Leaching solution manufacturing method according to existing official testing method (Lancaster method, based on 20 L of solution)
① Dissolve 400 mL of acetic acid ($CH_3COOH$) and 300 mL of 10-N lactic acid ($CH_3CH(OH)COOH$) in 6 L of distilled water.
② Dissolve 22.0 g of ammonium fluoride ($NH_4F$) in approximately 1 L of distilled water.
③ Dissolve 133.3 g of ammonium sulfate (($NH_4)_2SO_4$) in approximately 1 L of distilled water.
④ Dissolve 170 g of sodium hydroxide (NaOH) in approximately 2 L of distilled water.
⑤ Upon cooling to room temperature, add distilled water to reach a volume of 20 L.
⑥ Adjust to pH 4.25 ± 0.05 (adjust by dil acetic acid and dil sodium Hydroxide).

2. Preparation of Leaching Solution Composition for Extracting Available Silicate in Soil As shown in Table 2 below, for the manufacturing of 100 kg of a leaching solution for available silicate, 93,000 g of distilled water was first added into a 120-L reactor, and then 1,650 g of sodium acetate anhydrous ($CH_3COONa$) and 5,681.5 g of acetic acid ($CH_3COOH$) were added, followed by agitation at 100 rpm for 30 minutes, and then the pH was adjusted to 4.00 by using sodium acetate anhydrous ($CH_3COONa$) and acetic acid ($CH_3COOH$). In addition, 1 g of a methyl orange indicator was dissolved in a mixture of 100 g of ethanol and 100 g of distilled water, and then added together into the 120-L reactor, followed by further agitation for 1 minute, thereby manufacturing a leaching solution for available silicate. The pH of the leaching solution for available silicate was adjusted to 4.00±0.05, and for color distinguishment, 0.001 parts by weight of a methyl orange acid-base indicator was added relative to the entire weight (100 parts by weight) of the manufactured leaching solution for available silicate. The methyl orange indictor is characterized by showing an evident color change in a pH range of 4.00±0.05. The leaching solution for available silicate, to which the indicator has been added, exhibits a yellow-pink color, turns into dark pink if contaminated or denatured to have a pH of 4.00 or lower and thus be acidic, and turns into dark yellow if contaminated or denatured to have a pH of 4.00 or higher and thus be basic. When the methyl orange indicator is added in less than 0.001 parts by weight, the color of the leaching solution becomes thin, resulting in difficulty in color distinguishment with the naked eye. When the methyl orange indicator is added in more than 0.001 parts by weight, the color of the leaching solution becomes thick, which acts an obstacle in analysis. The concentration of the methyl orange indicator is most preferably 0.001 parts by weight.

The leaching solution for available silicate, to which the indicator has been added, exhibits a yellow-pink color at a normal state, turns into dark pink if contaminated or denatured to have a pH of 4.00 or lower and thus be acidic, and turns into dark yellow if contaminated or denatured to have a pH of 4.00 or higher and thus be basic. Therefore, the normal and contaminated states of the leaching solution for available silicate can be distinguished by colors.

TABLE 2

| Based on 100 kg of solution manufacturing | | |
|---|---|---|
| Leaching solution | Reagent | Amount |
| Leaching solution for available silicate | Sodium acetate anhydrous ($CH_3COONa$) | 1650 g |
| | acetic acid ($CH_3COOH$) | 5681.5 g | cf. Method of manufacturing a leaching solution for available silicate according to existing official testing method (1N-NaOAc leaching method, based on 20 L of solution)
49.2 mL of 1N-NaOAc acetic acid ($CH_3COOH$) and 14.8 g of sodium acetate ($CH_3COONa$) are mixed, and diluted to 1 L, and the pH is adjusted to 4.0 by using 1N-$CH_3COONa$ or 1N-$CH_3COOH$.

3. Preparation of Leaching Solution Composition for Extracting Exchangeable Cations in Soil As shown in Table 3 below, for the manufacturing of 100 kg of a leaching solution for exchangeable cations, 99,000 L of distilled water was first added into a 120-L reactor, and then 7.48 L of ammonia water ($NH_4OH$) and 7.315 L of acetic acid ($CH_3COOH$) were added, followed by agitation at 100 rpm for 30 minutes, and then the pH was adjusted to 7.00 by using ammonia water ($NH_4OH$) and acetic acid ($CH_3COOH$). In addition, the phenolphthalein and bromocresol purple indicators were each dissolved at 1 g in a mixture of 100 g of ethanol and 100 g of distilled water, and then added together into the 120-L reactor, followed by further agitation for 1 minute, thereby manufacturing a leaching solution for cation exchange. The pH of the leaching solution for cation exchange was adjusted to 7.00±0.05, and for color distinguishment, phenolphthalein and bromocresol purple indicators were each added in 0.001 parts by weight relative to the entire weight (100 parts by weight) of the leaching solution for exchangeable cations. The pH of the leaching solution for exchangeable cations was adjusted to 7.00±0.05, and for color distinguishment, the phenolphthalein and bromocresol purple acid-base indicators were each mixed and added in 0.001 parts by weight. The phenolphthalein and bromocresol purple indicators are characterized by showing evident color changes, which are different from each other, in a pH region of 7.00±0.05. The leaching solution for exchangeable cations, to which the indicators have been added, exhibits no color, and the leaching solution for exchangeable cations responds to the bromocresol purple indicator to turn into blue if contaminated or denatured to have a pH of 7.00 or lower and thus be acidic. The leaching solution for exchangeable cations responds to the phenolphthalein indicator to turn into red if contaminated or denatured to have a pH of 7.00 or higher and thus be basic. When the phenolphthalein and bromocresol purple indicators each are added in less than 0.001 parts by weight, the color of the leaching solution becomes thin, resulting in difficulty in color distinguishment. When the phenolphthalein and bromocresol purple indicators each are added in more than 0.001 parts by weight, the color of the leaching solution becomes thick, which acts an obstacle in analysis. Each of the concentrations of the phenolphthalein and bromocresol purple indicators is most preferably 0.001 parts by weight.

The leaching solution for exchangeable cations exhibits no color at a normal state, exhibits a blue color if contaminated by an acid, and exhibits a red color if contaminated by a base. Therefore, the normal and contaminated states of the leaching solution for exchangeable cations can be distinguished by colors.

TABLE 3

| Based on 100 kg of solution manufacturing | | |
|---|---|---|
| Leaching solution | Reagent | Volume |
| Leaching solution for exchangeable cations | Ammonia water (NH$_4$OH) | 7.48 L |
| | Acetic acid (CH$_3$COOH) | 7.315 L | cf. Method of manufacturing leaching solution for exchangeable cations according to existing official testing method (ammonia acetate method, based on 20 L of solution)
(1) Method of manufacturing a leaching solution (1N-NH$_4$OAc) by using NH$_4$OH and CH$_3$COOH
① Dilute 1.3 6 L of ammonia water (NH$_4$OH) in 10 L of distilled water, and separately, 1.13 L of acetic acid (CH$_3$COOH) in 10 L of distilled water.
② Mix the two solutions to lead to 20 L and adjust pH to 7.00 accurately.
③ Adjust pH by dil CH$_3$COOH and NH$_4$OH if the pH is not 7.00.

As set forth above, the present disclosure has been described based on preferred examples and comparative examples, but the technical idea of the present disclosure is not limited thereto, and it would be obvious to a person having ordinary knowledge in the art to which the present disclosure pertains that variations and modifications may be implemented within the scope of claims, and such variations and modifications would fall into the scope of the appended claims.

What is claimed is:

1. A leaching solution composition for extracting available phosphate in soil, the composition comprising:
   100 parts by weight of a leaching solution containing acetic acid, lactic acid, ammonium fluoride, ammonium sulfate, and sodium hydroxide, of which the weights are 110% of the weights of acetic acid, lactic acid, ammonium fluoride, ammonium sulfate, and sodium hydroxide, respectively, contained in a leaching solution for extracting available phosphate in soil, used in the Lancaster method; and
   0.001 parts by weight of a bromocresol green indicator.

\* \* \* \* \*